(12) United States Patent
Davies et al.

(10) Patent No.: US 7,622,076 B2
(45) Date of Patent: Nov. 24, 2009

(54) MICROFLUIDIC ANALYSIS SYSTEM

(75) Inventors: Mark Davies, Limerick (IE); Tara Dalton, Limerick (IE)

(73) Assignee: Stokes Bio Limited, Limerick (IE)

( * ) Notice: Subject to any disclaimer, the term of this patent is extended or adjusted under 35 U.S.C. 154(b) by 367 days.

(21) Appl. No.: 11/366,524

(22) Filed: Mar. 3, 2006

(65) Prior Publication Data

US 2006/0205062 A1 Sep. 14, 2006

Related U.S. Application Data

(63) Continuation of application No. PCT/IE2004/000115, filed on Sep. 6, 2004.

(60) Provisional application No. 60/500,344, filed on Sep. 5, 2003, provisional application No. 60/500,345, filed on Sep. 5, 2003.

(51) Int. Cl.
*G01N 21/00* (2006.01)
(52) U.S. Cl. ...................................................... 422/57
(58) Field of Classification Search .................... 422/57
See application file for complete search history.

(56) References Cited

U.S. PATENT DOCUMENTS

| 5,270,183 | A * | 12/1993 | Corbett et al. ............. 435/91.2 |
| 6,294,063 | B1 * | 9/2001 | Becker et al. ............... 204/450 |
| 6,306,590 | B1 | 10/2001 | Mehta et al. ................... 435/6 |
| 6,670,153 | B2 | 12/2003 | Stern ......................... 435/91.2 |
| 2003/0170698 | A1 * | 9/2003 | Gascoyne et al. ............... 435/6 |

FOREIGN PATENT DOCUMENTS

| WO | WO99/41015 | 8/1999 |
| WO | WO03/016558 | 2/2003 |

OTHER PUBLICATIONS

Yang J.; Huang, Y.; Wang, X.-B.; Becker, F. F.; Gascoyne, R.C. "Cell Separation on Microfabricated Electrodes Using Dielectrophoretic/Gravitational Field-Flow Fractionation." Anal. Chem. 1999, 71, pp. 91-918.*

* cited by examiner

*Primary Examiner*—Walter D Griffin
*Assistant Examiner*—Bobby Ramdhanie
(74) *Attorney, Agent, or Firm*—Thomas C. Meyers; Adam M. Schoen; Brown Rudnick LLP

(57) ABSTRACT

A microfluidic analysis system (1) performs polymerase chain reaction (PCR) analysis on a bio sample. In a centrifuge (6) the sample is separated into DNA and RNA constituents. The vortex is created by opposing flow of a silicon oil primary carrier fluid effecting circulation by viscous drag. The bio sample exits the centrifuge enveloped in the primary carrier fluid. This is pumped by a flow controller (7) to a thermal stage (9). The thermal stage (9) has a number of microfluidic devices (70) each having thermal zones (71, 72, 73) in which the bio sample is heated or cooled by heat conduction to/from a thermal carrier fluid and the primary carrier fluid. Thus, the carrier fluids envelope the sample, control its flowrate, and control its temperature without need for moving parts at the micro scale.

21 Claims, 6 Drawing Sheets

MICROFLUIDIC ANALYSIS SYSTEM

This is a CONTINUATION of PCT/IE2004/000115 filed 6 Sep. 2004 and published in English, claiming the priorities of U.S. Application No. 60/500,344 and 60/500,345, both filed on 5 Sep. 2003.

INTRODUCTION

1. Field of the Invention

The invention relates to analysis systems for analysis such as Polymerase Chain Reaction (PCR) analysis to detect the population of rare mutated cells in a sample of bodily fluid and/or tissue.

2. Prior Art Discussion

It is known for at least the past decade that cancers have a genetic cause. With the emergence of fast methods of sequencing and the publication of the human genome, the motivation and methods are available to find the genetic causes, both germline and somatic, of the most prevalent cancers. Contemporary oncological research suggests that there is a sequence of mutations that must occur for a cancer to be life-threatening, called the multistage model. Cancer could therefore be diagnosed earlier by detecting these genetic markers thereby increasing the probability of cure. However, even with refining of the sample, the target cells and their DNA are still usually very rare, perhaps one part in $10^6$. The analysis system must therefore be able to perform very effective amplification.

There are several methods of attempting to identify rare cells in a sample of bio-fluid. A common method is to probe the sample using known genetic markers, the markers being specific to the type of mutation being sought, and then amplify the targets in the sample. If the mutations or chromosomal aberrations are present then the amplification can be detected, usually using optical techniques.

It is also possible, depending on the amplification used, to use the Polymerase Chain Reaction (PCR) to detect the number of mutated cells in the original sample: a number important as firstly, it can be linked to the progress of the cancer and secondly, it provides a quantitative measure with which to diagnose remission. PCR is the enzyme-catalysed reaction used to amplify the sample. It entails taking a small quantity of DNA or RNA and producing many identical copies of it in vitro. A system to achieve a PCR is to process the samples by thermally cycling them is described in U.S. Pat. No. 5,270,183. However, this apparently involves a risk of sample contamination by surfaces in the temperature zones and other channels. Also, U.S. Pat. No. 6,306,590 describes a method of performing a PCR in a microfluidic device, in which a channel heats, and then cools PCR reactants cyclically. U.S. Pat. No. 6,670,153 also describes use of a microfluidic device for PCR.

The invention is directed towards providing an improved microfluidic analysis system for applications such as the above.

SUMMARY OF THE INVENTION

According to the invention, there is provided a biological sample analysis system comprising:
  a carrier fluid;
  a sample supply;
  a sample preparation stage for providing a flow of sample enveloped in a primary carrier fluid;
  at least one analysis stage for performing analysis of the sample while controlling flow of the sample while enveloped within the primary carrier fluid without the sample contacting a solid surface; and
  a controller for controlling the system.

In one embodiment, the analysis stages comprise a thermal cycling stage and an optical detection stage for performance of a polymerise chain reaction.

In another embodiment, the sample preparation stage comprises a centrifuge for separation of samples from an input fluid and for introduction of the samples to the primary carrier fluid.

In a further embodiment, the centrifuge comprises a pair of opposed primary carrier fluid channels on either side of a vortex chamber, whereby flow of primary carrier fluid in said channels causes centrifuging of sample in the vortex chamber and flow of sample from the chamber into said channels.

In one embodiment, contact between the sample and the vortex chamber surface is avoided by wrapping the sample in an initial carrier fluid within the chamber.

In another embodiment, the controller directs separation in the centrifuge either radially or axially due to gravity according to nature of the input fluid such as blood containing the sample.

In a further embodiment, the primary carrier fluid velocity is in the range of 1 m/s to 20 m/s.

In one embodiment, the thermal cycling stage comprises a microfluidic thermal device comprising a thermal zone comprising a sample inlet for flow of sample through a sample channel while enveloped in the primary carrier fluid, and a thermal carrier inlet for flow of a thermal carrier fluid to heat or cool the sample by heat conduction through the primary carrier fluid.

In another embodiment, the microfluidic thermal device thermal zone further comprises separate sample and thermal outlets positioned to allow flow of thermal carrier fluid into and out of contact with the primary carrier fluid.

In a further embodiment, there is at least one pair of opposed thermal carrier inlet/outlet pairs on opposed sides of a sample channel.

In one embodiment, the thermal cycling stage comprises a plurality of thermal zones.

In one embodiment, the microfluidic thermal device comprises a plurality of thermal zones in series.

In another embodiment, the thermal cycling stage comprises a plurality of microfluidic thermal devices in series.

In a further embodiment, the microfluidic thermal device comprises a closed sample channel for re-circulation of sample with successive heating or cooling in successive thermal zones.

In one embodiment, the controller directs flow of the thermal and primary carrier fluids to control flowrate of sample by enveloping within the primary carrier fluid and by viscous drag between the thermal carrier fluid and the primary carrier fluid.

In another embodiment, the primary carrier fluid is biologically non-reactive.

In a further embodiment, the primary carrier fluid is a silicone oil.

In one embodiment, the thermal carrier fluid is biologically non-reactive.

In another embodiment, the thermal carrier fluid is a silicone oil.

In a further embodiment, the temperatures and flowrates of the carrier fluids are controlled to achieve a temperature ramping gradient of 17° C./sec to 25° C./sec.

BRIEF DESCRIPTION OF THE DRAWINGS

The invention will be more clearly understood from the following description of some embodiments thereof, given by way of example only with reference to the accompanying drawings in which:—

DESCRIPTION OF THE EMBODIMENTS

Figure 1:
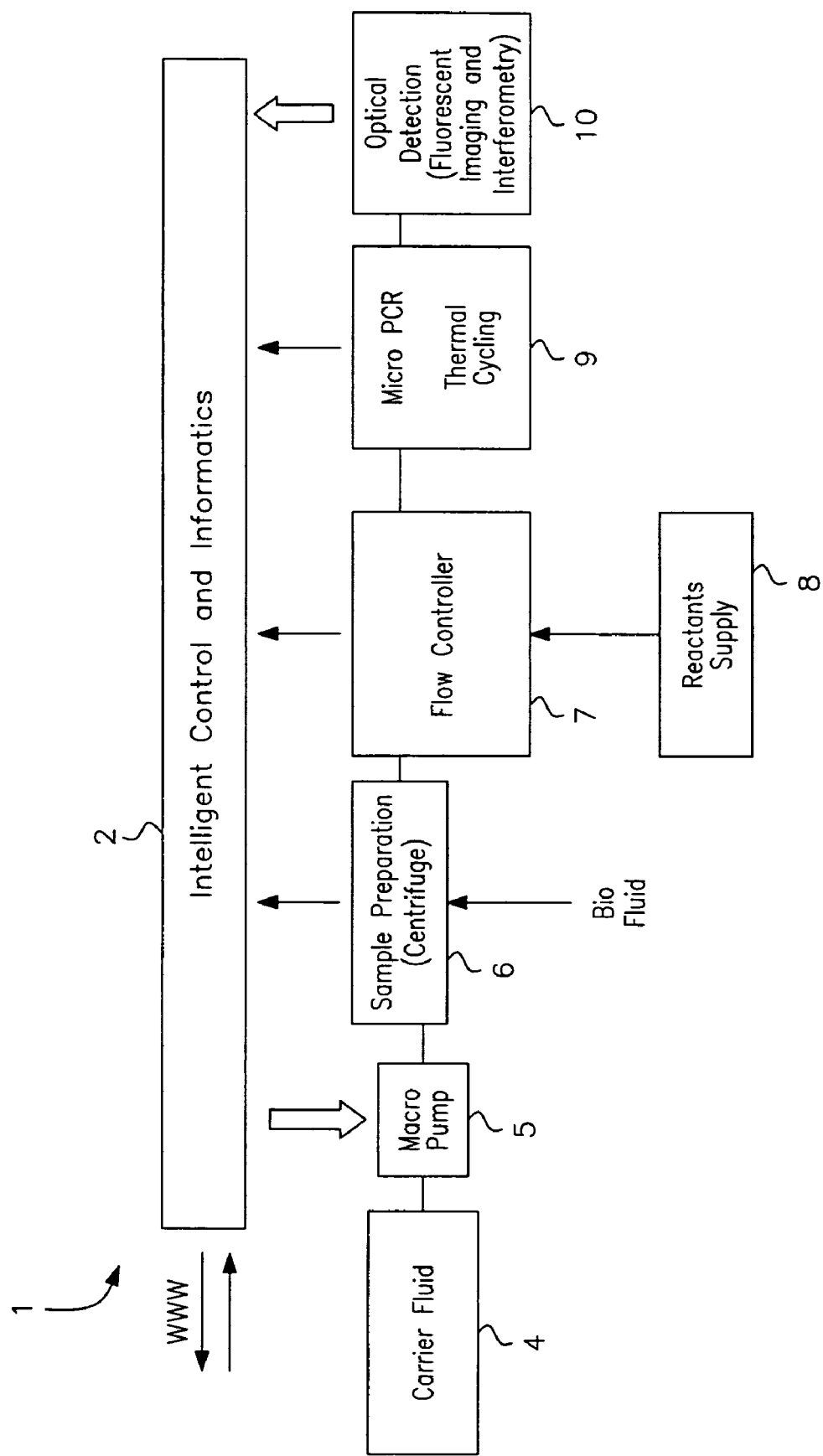
FIG. 1 is a diagram of an analysis system of the invention.

Referring to FIG. 1 an analysis system 1 comprises a controller 2 which interfaces with various stages. A carrier fluid supply 4 delivers carrier fluid to a macro pump 5 which delivers it at a high flowrate to a sample preparation stage 6. The latter also receives a bio-fluid sample, and centrifuges the sample in a vortex created by carrier fluid flow, as described in more detail below. Reactants are supplied by a supply 8 to a flow controller 7 which delivers streams of separated DNA with reactants enveloped in carrier fluid to a thermal cycling stage 9. The DNA is amplified in the stage 9 and optically detected by a detection stage 10. Throughout the process the samples are enveloped in a biologically non-reactive carrier fluid such as silicone oil. This avoids risk of contamination from residual molecules on system channel surfaces.

Figure 2:
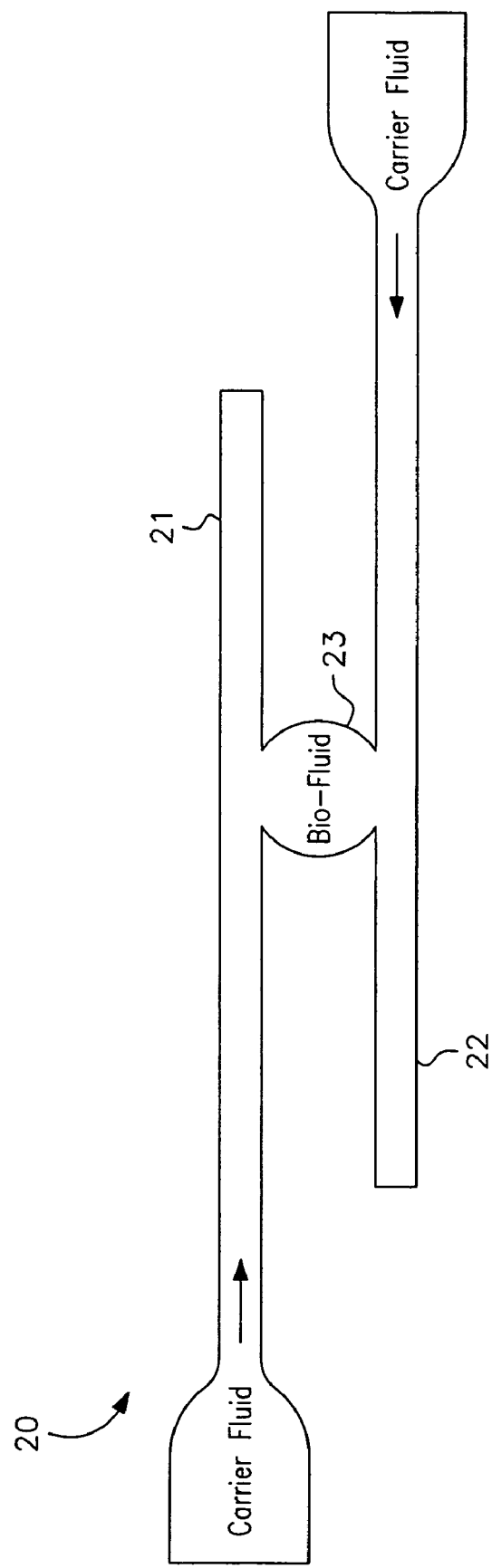
FIG. 2 is a diagrammatic plan view of a centrifuge of the system.

Referring to FIG. 2 a centrifuge device 20 of the sample preparation stage 6 is illustrated diagrammatically. It comprises opposed carrier supply lines 21 and 22 and a central vortex chamber 23 having a sample inlet out of the plane of the page. The centrifuge 20 operates by primary carrier fluid in the channels 21 and 22 driving sample fluid in the chamber 23 into a vortex via viscous forces at the interface between the two fluids. In this embodiment, the carrier fluid is silicone oil mixed to be neutrally buoyant with the sample.

Figure 3:
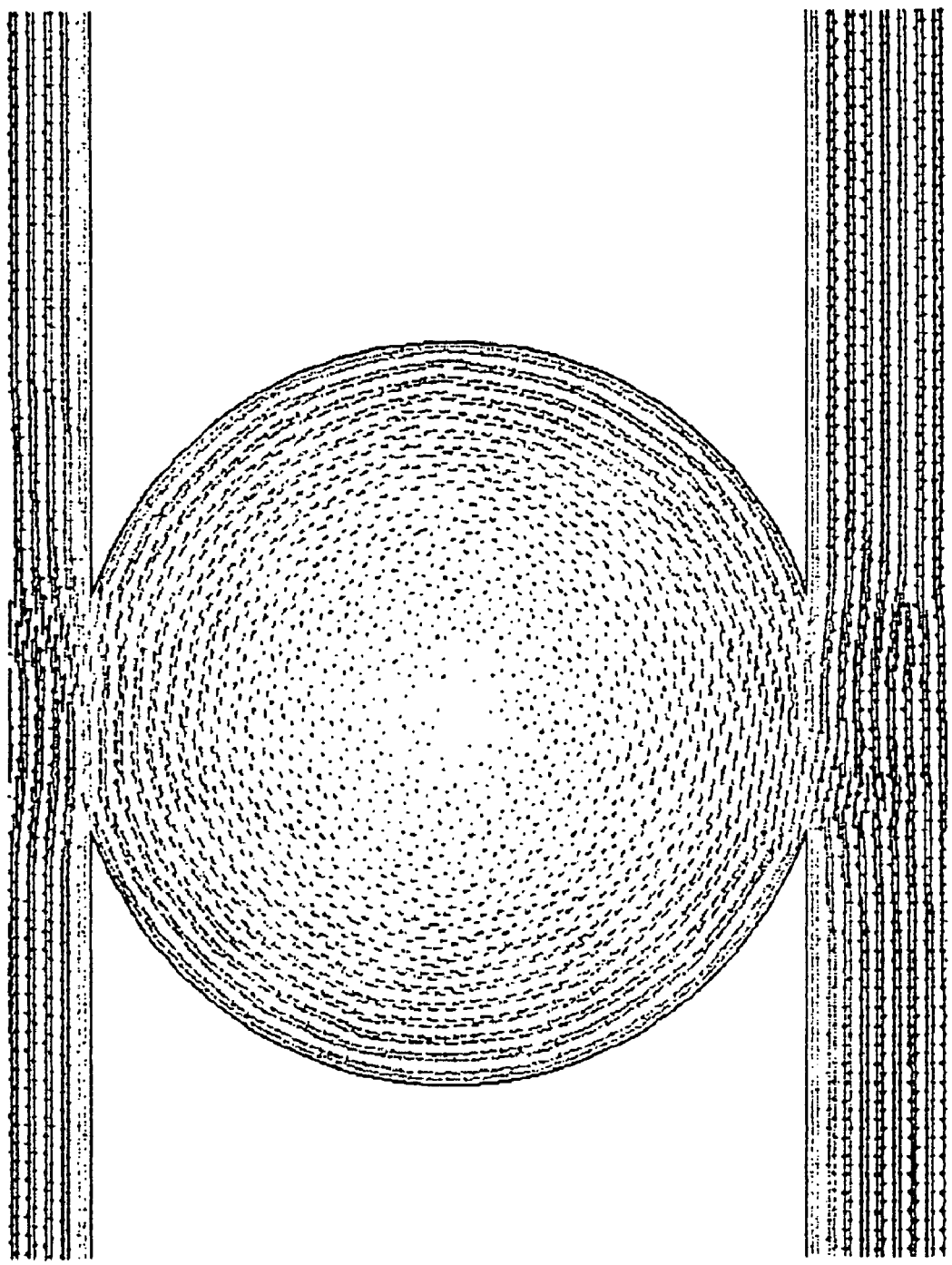
FIG. 3 is a simulation diagram showing centrifuging.

The vortex, or centrifuge, is thus established without any mechanical moving parts. The carrier fluid drives a vortex of the sample to be centrifuged thereby avoiding the very many difficulties of designing and operating moving parts at the micro scale, particularly at high rotational speeds. FIG. 3 illustrates the centrifuging activity, the greater density of dots indicating higher flow velocities. The left-hand scale shows the velocity range of 1 m/s to 20 m/s. The sample is wrapped in an initial volume of carrier fluid within the chamber 23 to prevent surface contamination.

This achieves a continuous throughput micro-centrifuging to suitably extract DNA and RNA from cellular material. The bio-fluid is centrifuged resulting in DNA and other bio-molecules of interest accumulating at the bottom of the chamber, thereby providing an efficient and simple method of manipulating micron and sub-micron quantities of bio-fluid. The DNA and RNA are separated due to the greater weight and viscous resistance of the DNA. Numerical simulations (FIG. 3) of the flow show that tangential velocities of up to 10 ms$^{-1}$ are generated towards the edge of the vortex core. Calculations reveal this to be equivalent to a rotational speed of almost 20,000 rpm or 2,000 g in terms of a centrifugal force. In order to achieve these levels of centrifugal force, the carrier fluid is pumped at speeds of 5 ms$^{-1}$ through the system. In general, the desired carrier fluid speed is 1 m/s to 20 m/s. The device has further potential to be miniaturized to centrifuge at up to 200,000 g, as these levels of force are necessary for efficient separation of RNA and other smaller cellular constituents and bio-molecules.

Overall, the continuous throughput centrifuge offers many benefits over conventional technology. The device may also function as a fluid mixing device by reversing the flow path of one of the carrier fluid, if such is desired for an application. It is modular in nature, meaning two or more systems can be placed together in any configuration and run by the same control and power source system. The centrifuge 20 has no moving parts thereby allowing excellent reliability compared with a system having moving parts. An important consequence of this feature is that manufacturing this device at the micro-scale using current silicon processing or micro-machining is readily achievable.

Figure 4:
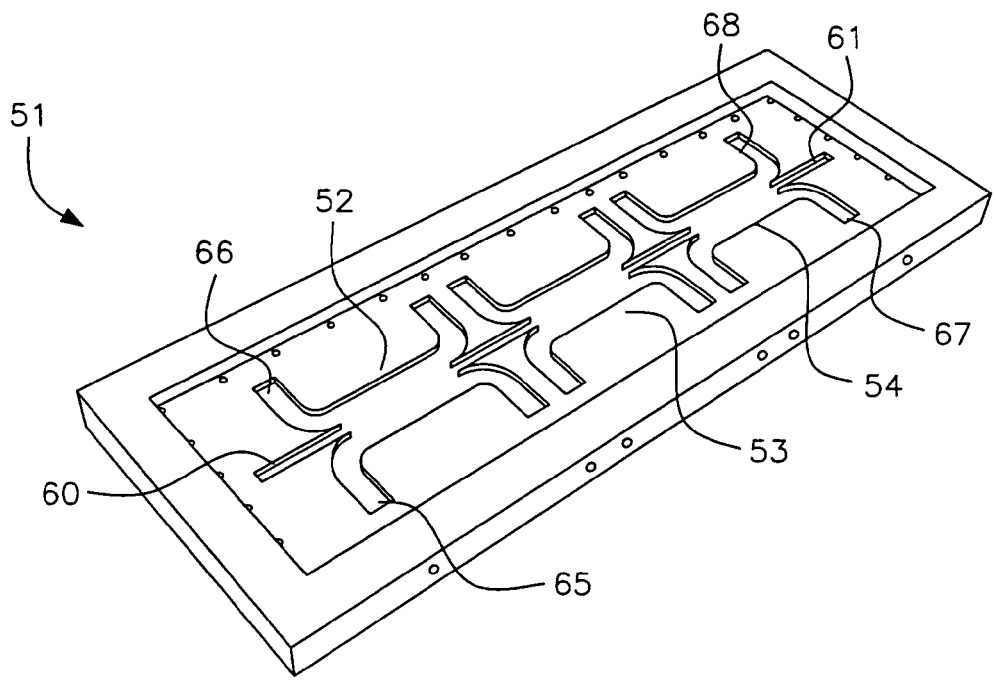
FIG. 4 is a perspective view of the main body of a microfluidic heater of the system.

Referring to FIG. 4 a microfluidic thermal device 51 of the stage 9 is shown. It comprises three successive thermal zones 52, 53, and 54. Each zone comprises a sample inlet 60 and an outlet 61 for flow of the bio sample in the primary carrier fluid. There are also a pair of thermal carrier inlets 65 and 66, and a pair of thermal carrier outlets 67 and 68 for each of the three zones. This drawing shows only the main body, there also being top and bottom sealing transparent plates.

The bio sample which enters the sample inlet 60 of each stage is enveloped and conveyed by the carrier fluid henceforth called the "primary carrier fluid". Thermal carrier fluid is delivered at the inlets 65 and 66 to heat or cool the bio sample via the primary carrier fluid.

As the sample remains in a low shear rate region of the flow, mass transport by diffusion of sample species is kept to a minimum. The low shear region reduces damage by shear to macro molecules that may be carried by the bio sample. The arrangement of a number (in this case three) of thermal zones in series offers advantages to applications such as the polymerase chain reaction (PCR) where rapid and numerous thermal cycles lead to dramatic amplification of a DNA template strand.

The device 51 also acts as an ejector pump, in which the velocity and hence the residency time of the sample is controlled by controlling velocity of one or both of the carriers fluids. The carrier flow parameters determine how long the sample remains at the set temperature in each zone. This is often important, as chemical reactions require particular times for completion. The device 51 can therefore be tuned to the required residency times and ramp rates by controlling the carrier velocity.

Figure 5:
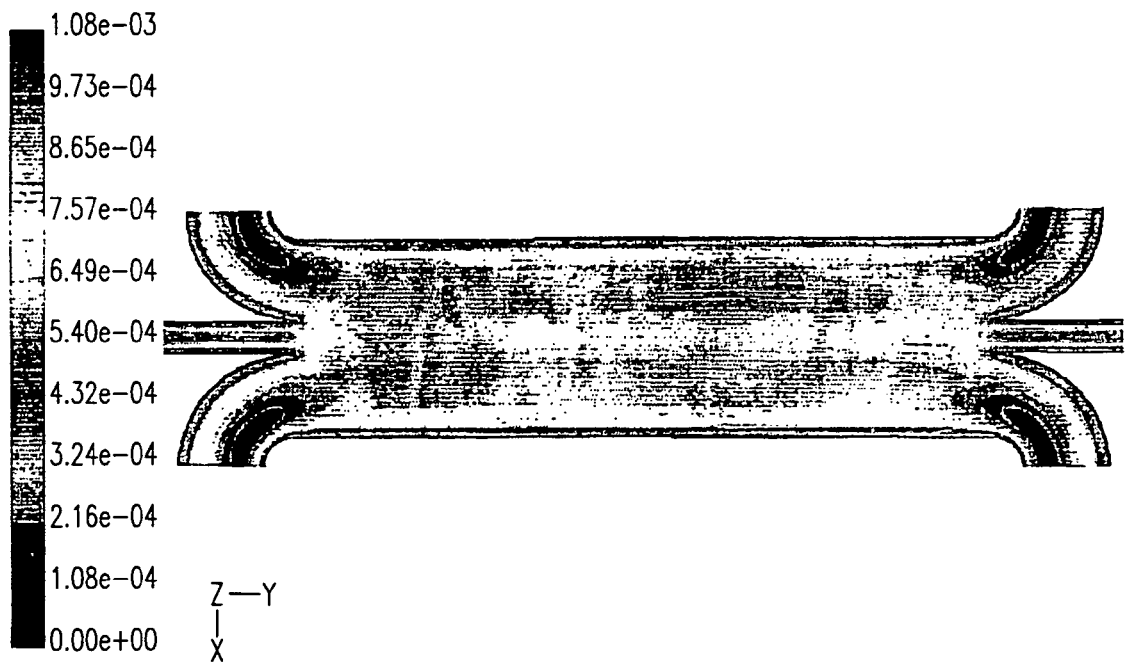
FIG. 5 is a prediction velocity and temperature plot along a thermal stage of the heater.

Referring to FIG. 5 a predicted velocity contour map at the mid-height plane of a zone channel is shown. Carrier fluid enters through the channels at the top and bottom left of the image and exits through the channels at the top and bottom right of the image. The sample fluid enters and exits through the central channel. The different shadings of this map indicate the velocities, the range being 0.01 m/s to 0.1 m/s.

In one example, sample fluid enters through the central channel at the left of the image at a temperature of 50° C. and is heated to 70° C. by the thermal carrier fluid.

Figure 6:
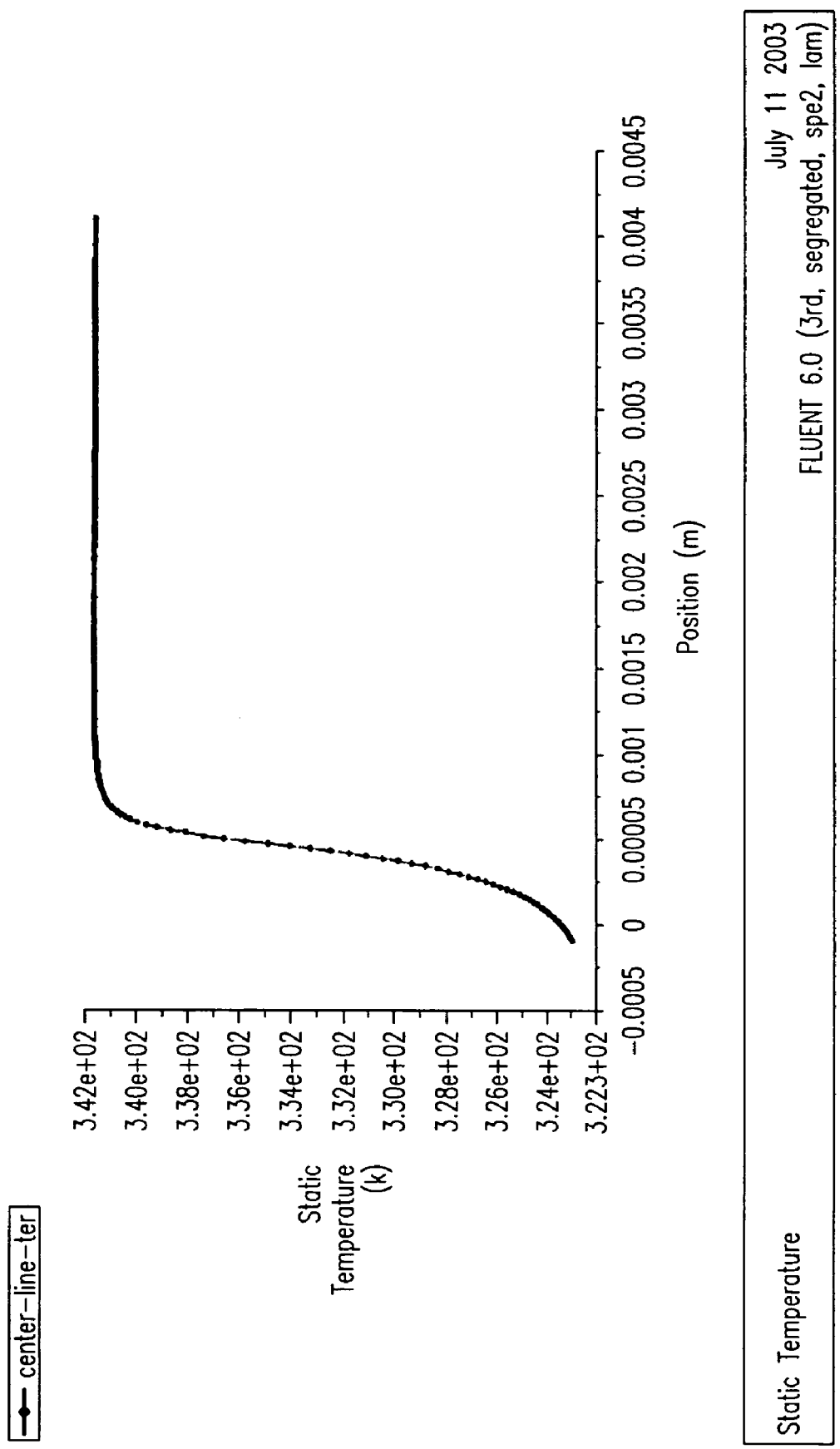
FIG. 6 is a centre line temperature profile in the flow direction showing fast response of same in the heated zone.

FIG. 6 shows a temperature profile along a longitudinal centreline of a thermal zone. A target temperature of 342 K is achieved within an extremely short distance from entrance, achieving an excellent temperature ramp rate of 20° C./sec over a distance of 0.05 m. In general, a ramping of 17° C./sec to 25° C./sec is desirable for many applications.

The following table sets out parameters for one example. A silicone oil, density matched to the density of the bio sample, is used for both of the carrier fluids.

TABLE 1

Boundary Conditions and Fluid Properties

| | |
|---|---|
| Overall Channel Dimensions | 5 mm × 5 mm × 200 mm |
| Wall Boundary Condition outside of carrier flow interaction zones | Adiabatic |
| Heat Transfer Carrier Fluid Inlet temperature | 70° C., 90° C., 100° C. for each zone |
| Sample/Transport Carrier Inlet Pressure | 0 Pa |
| Heat Transfer Carrier Fluid Inlet Pressure | 0.2 Pa |
| Sample/Transport Carrier Outlet Pressure | 1.9 Pa |
| Heat Transfer Carrier Fluid Outlet Pressure | 1.7 Pa |
| Mass Diffusivity | 1.3E−12 m$^2$/s |
| Approximate Temperature Gradient in Zones | 20° C./sec |

Figure 7:
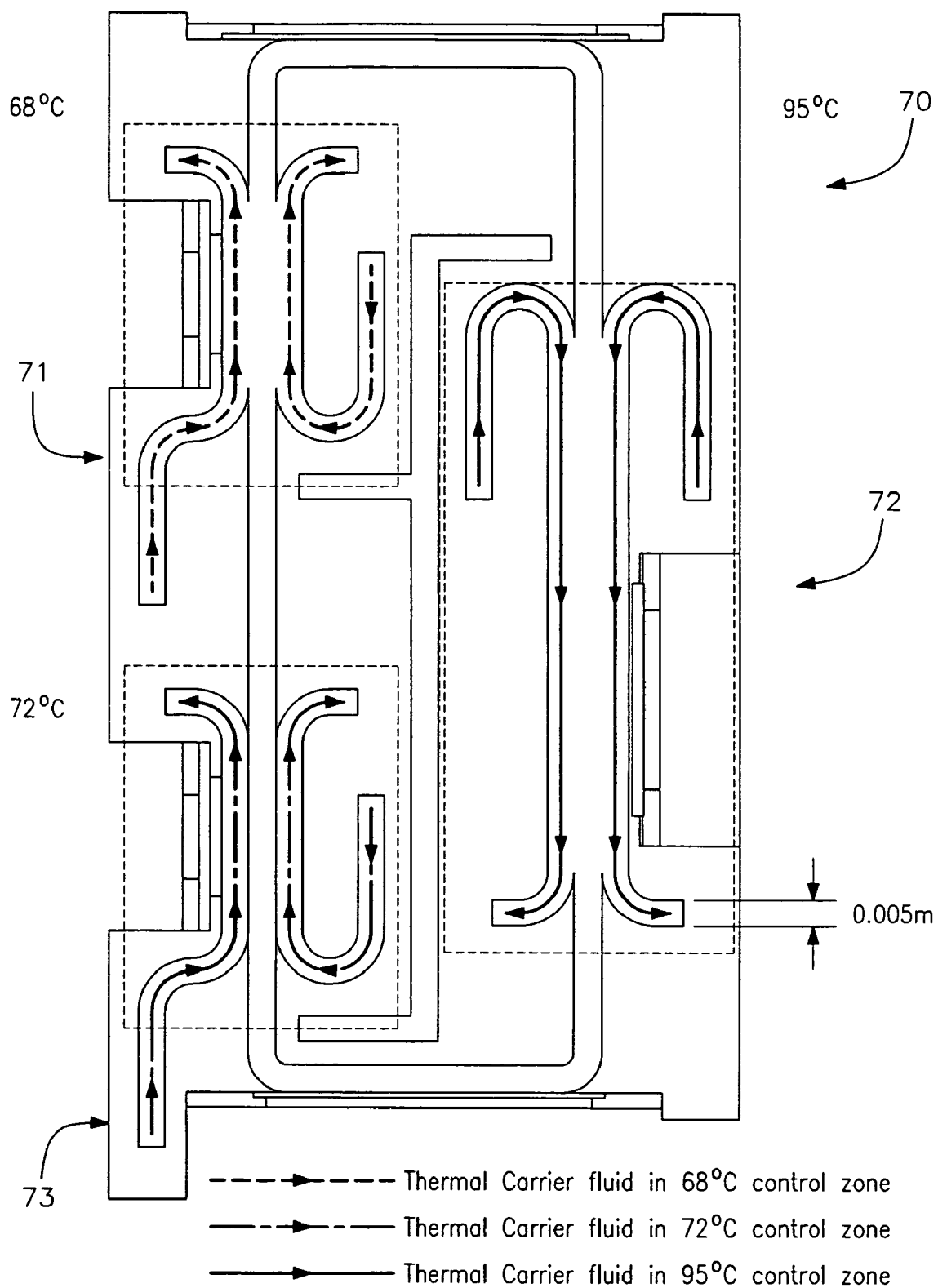
FIG. 7 is a plan view of an alternative microfluidic heater.

Referring to FIG. 7, another microfluidic thermal device, 70, is shown. There are again three thermal zones, however in this case on a generally rectangular closed circuit, with zones 71, 72, and 73. The zones 71 and 73 are on one side and there is only a single zone, 72, on the other side. The thermal carrier fluid is silicone oil, as is the primary carrier fluid. The thermal carrier fluid for the zone 71 is at 68° C., to ramp up the bio sample to this temperature during residency in this zone. The zones 72 and 73 provide outlet temperatures of 95° C. and 72° C. respectively.

The optical detection stage 10 is positioned over the microfluidic device 70 to analyse the sample. The silicone oil is sufficiently transparent to detect the fluorescently tagged molecules.

It will be appreciated that the invention achieves comprehensive control over bio sample flowrate and temperature, with no risk of contamination from device surfaces. The invention also achieves integrated pumping and thermal cycling of the sample without moving parts at the microscale. There are very high throughputs as measured by processing time for one sample.

The system is expected to have a low cost and high reliability due to the absence of micro scale moving parts. The system also allows independent control and variation of all PCR parameters for process optimisation.

The invention is not limited to the embodiments described but may be varied in construction and detail.

The invention claimed is:

1. A biological sample analysis system comprising:
   a carrier fluid supply;
   a sample supply;
   a sample preparation stage for providing a flow of sample droplets enveloped in an immiscible primary carrier fluid;
   at least one channel for continuous flow of the carrier fluid which carries the sample droplets;
   at least one analysis stage for performing analysis of the sample droplets while continuously enveloped within the primary carrier fluid without the sample droplets contacting a solid surface of the channel; and
   a controller for controlling the system.

2. The biological sample analysis system as claimed in claim 1, wherein there are a plurality of analysis stages, and said analysis stages comprise a thermal cycling stage and an optical detection stage for performance of a polymerase chain reaction.

3. The biological sample analysis system as claimed in claim 1, wherein there are a plurality of analysis stages, and said analysis stages comprise a thermal cycling stage and an optical detection stage for performance of a polymerase chain reaction; and wherein the sample preparation stage comprises a centrifuge for separation of samples from an input fluid and for introduction of the samples to the primary carrier fluid.

4. A biological sample analysis system comprising:
   a carrier fluid supply;
   a sample supply;
   a sample preparation stage for providing a flow of sample droplets enveloped in an immiscible primary carrier fluid;
   at least one channel for continuous flow of the carrier fluid which carries the sample droplets;
   at least one analysis stage for performing analysis of the sample in the continuous flow while enveloped within the primary carrier fluid without the sample contacting a solid surface of the channel; and
   a controller for controlling the system,
   wherein there are a plurality of analysis stages, and said analysis stages comprise a thermal cycling stage and an optical detection stage for performance of a polymerase chain reaction;
   wherein the sample preparation stage comprises a centrifuge for separation of samples from an input fluid and for introduction of the samples to the primary carrier fluid; and wherein the centrifuge comprises a pair of opposed primary carrier fluid channels on either side of a vortex chamber, whereby flow of primary carrier fluid in said channels causes centrifuging of sample in the vortex chamber and flow of sample from the chamber into said channels.

5. The biological sample analysis system as claimed in claim 4, wherein contact between the sample and the vortex chamber surface is avoided by wrapping the sample in an initial carrier fluid within the chamber.

6. The biological sample analysis system as claimed in claim 3, wherein the controller directs separation in the centrifuge either radially or axially due to gravity according to nature of the input fluid such as blood containing the sample.

7. The biological sample analysis system as claimed in claim 4, wherein the primary carrier fluid velocity is in the range of 1 m/s to 20 m/s.

8. The biological sample analysis system as claimed in claim 2, wherein the thermal cycling stage comprises a microfluidic thermal device comprising a thermal zone comprising a sample inlet for flow of sample through a sample channel while enveloped in the primary carrier fluid, and a thermal carrier inlet for flow of a thermal carrier fluid to heat or cool the sample by heat conduction through the primary carrier fluid.

9. The biological sample analysis system as claimed in claim 2, wherein the thermal cycling stage comprises a microfluidic thermal device comprising a thermal zone comprising a sample inlet for flow of sample through a sample channel while enveloped in the primary carrier fluid, and a thermal carrier inlet for flow of a thermal carrier fluid to heat or cool the sample by heat conduction through the primary carrier fluid; and
   wherein the microfluidic thermal device thermal zone further comprises separate sample and thermal outlets positioned to allow flow of thermal carrier fluid into and out of contact with the primary carrier fluid.

10. The biological sample analysis system as claimed in claim 2, wherein the thermal cycling stage comprises a microfluidic thermal device comprising a thermal zone comprising a sample inlet for flow of sample through a sample channel while enveloped in the primary carrier fluid, and a thermal carrier inlet for flow of a thermal carrier fluid to heat or cool the sample by heat conduction through the primary carrier fluid;

wherein the microfluidic thermal device thermal zone further comprises separate sample and thermal outlets positioned to allow flow of thermal carrier fluid into and out of contact with the primary carrier fluid; and wherein there is at least one pair of opposed thermal carrier inlet/outlet pairs on opposed sides of a sample channel.

11. The biological sample analysis system as claimed in claim 2, wherein the thermal cycling stage comprises a microfluidic thermal device comprising a thermal zone comprising a sample inlet for flow of sample through a sample channel while enveloped in the primary carrier fluid, and a thermal carrier inlet for flow of a thermal carrier fluid to heat or cool the sample by heat conduction through the primary carrier fluid; and wherein the thermal cycling stage comprises a plurality of thermal zones.

12. The biological sample analysis system as claimed in claim 11, wherein the microfluidic thermal device comprises a plurality of thermal zones in series.

13. The biological sample analysis system as claimed in claim 2, wherein the thermal cycling stage comprises a microfluidic thermal device comprising a thermal zone comprising a sample inlet for flow of sample through a sample channel while enveloped in the primary carrier fluid, and a thermal carrier inlet for flow of a thermal carrier fluid to heat or cool the sample by heat conduction through the primary carrier fluid; and wherein the thermal cycling stage comprises a plurality of microfluidic thermal devices in series.

14. The biological sample analysis system as claimed in claim 2, wherein the thermal cycling stage comprises a microfluidic thermal device comprising a thermal zone comprising a sample inlet for flow of sample through a sample channel while enveloped in the primary carrier fluid, and a thermal carrier inlet for flow of a thermal carrier fluid to heat or cool the sample by heat conduction through the primary carrier fluid; and wherein the microfluidic thermal device comprises a closed sample channel for re-circulation of sample with successive heating or cooling in successive thermal zones.

15. The biological sample analysis system as claimed in claim 2, wherein the thermal cycling stage comprises a microfluidic thermal device comprising a thermal zone comprising a sample inlet for flow of sample through a sample channel while enveloped in the primary carrier fluid, and a thermal carrier inlet for flow of a thermal carrier fluid to heat or cool the sample by heat conduction through the primary carrier fluid; and wherein the controller directs flow of the thermal and primary carrier fluids to control flowrate of sample by enveloping within the primary carrier fluid and by viscous drag between the thermal carrier fluid and the primary carrier fluid.

16. The biological sample analysis system as claimed in claim 1, wherein the primary carrier fluid is biologically non-reactive.

17. The biological sample analysis system as claimed in claim 16, wherein the primary carrier fluid is a silicone oil.

18. The biological sample analysis system as claimed in claim 2, wherein the thermal cycling stage comprises a microfluidic thermal device comprising a thermal zone comprising a sample inlet for flow of sample through a sample channel while enveloped in the primary carrier fluid, and a thermal carrier inlet for flow of a thermal carrier fluid to heat or cool the sample by heat conduction through the primary carrier fluid; and wherein the thermal carrier fluid is biologically non-reactive.

19. The biological sample analysis system as claimed in claim 18, wherein the thermal carrier fluid is a silicone oil.

20. The biological sample analysis system as claimed in claim 2, wherein the thermal cycling stage comprises a microfluidic thermal device comprising a thermal zone comprising a sample inlet for flow of sample through a sample channel while enveloped in the primary carrier fluid, and a thermal carrier inlet for flow of a thermal carrier fluid to heat or cool the sample by heat conduction through the primary carrier fluid; and wherein the temperatures and flowrates of the carrier fluids are controlled to achieve a temperature ramping gradient of 17° C./sec to 25° C./sec.

21. A biological sample analysis system comprising:

at least one channel for continuous flow of sample droplets enveloped in an immiscible carrier fluid, wherein the droplets do not contact a surface of the channel; and an analysis stage for analyzing the sample droplets while the droplets are flowing through the channel.

* * * * *

UNITED STATES PATENT AND TRADEMARK OFFICE
CERTIFICATE OF CORRECTION

| | |
|---|---|
| PATENT NO. | : 7,622,076 B2 |
| APPLICATION NO. | : 11/366524 |
| DATED | : November 24, 2009 |
| INVENTOR(S) | : Davies et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 633 days.

Signed and Sealed this

Twenty-sixth Day of October, 2010

David J. Kappos
*Director of the United States Patent and Trademark Office*